(12) United States Patent
Moenkemoeller

(10) Patent No.: US 9,322,774 B2
(45) Date of Patent: Apr. 26, 2016

(54) GAS-SENSOR ARRANGEMENT FOR DETECTING TARGET-GAS CONCENTRATION

(71) Applicant: paragon ag, Delbrueck (DE)

(72) Inventor: Ralf Moenkemoeller, Delbrueck (DE)

(73) Assignee: paragon AG, Delbrueck (DE)

( * ) Notice: Subject to any disclaimer, the term of this patent is extended or adjusted under 35 U.S.C. 154(b) by 0 days.

(21) Appl. No.: 14/792,720

(22) Filed: Jul. 7, 2015

(65) Prior Publication Data

US 2016/0018321 A1  Jan. 21, 2016

(30) Foreign Application Priority Data

Jul. 19, 2014  (DE) .......................... 10 2014 010 713

(51) Int. Cl.
*G01J 5/02* (2006.01)
*G01N 21/3504* (2014.01)
*G01N 33/00* (2006.01)

(52) U.S. Cl.
CPC .......... *G01N 21/3504* (2013.01); *G01N 33/004* (2013.01); *G01N 2201/061* (2013.01)

(58) Field of Classification Search
CPC .... G01N 21/35; G01N 21/61; G01N 21/3504

USPC ....................................................... 250/341.1
See application file for complete search history.

(56) References Cited

U.S. PATENT DOCUMENTS 5,468,961 A * 11/1995 Gradon ................. A61M 16/16
                                                      250/343
5,886,348 A *  3/1999 Lessure ............. G01N 21/3504
                                                    250/339.03

* cited by examiner

*Primary Examiner* — David Porta
*Assistant Examiner* — Meenakshi Sahu
(74) *Attorney, Agent, or Firm* — Andrew Wilford

(57) ABSTRACT

An NDIR gas-sensor arrangement for measuring a target-gas concentration comprises a variable-power infrared-radiation emitter that can project radiant energy from one side of a space containing the target gas and through the space to the other side thereof, a infrared-radiation receiver on the other side of the space and positioned to be irradiated by the radiant energy projected by the emitter through the space for emitting a signal corresponding to radiation received, and a filter between the receiver and the space and permeable only to radiation of a wavelength range that corresponds to the target gas. A controller connected to the radiation receiver calculates the target-gas concentration on the basis of the signal from the receiver to the controller.

10 Claims, 1 Drawing Sheet

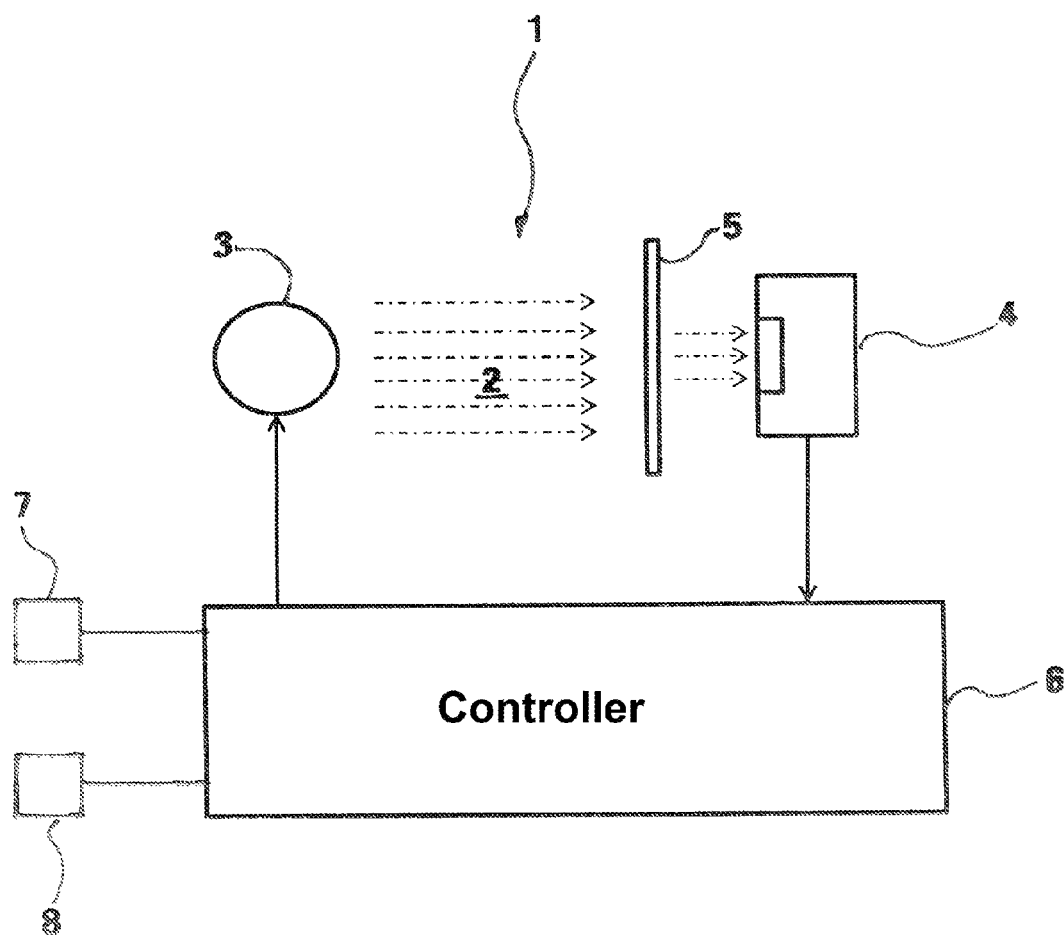

GAS-SENSOR ARRANGEMENT FOR DETECTING TARGET-GAS CONCENTRATION

FIELD OF THE INVENTION

The present invention relates to sensor arrangement. More particularly this invention concerns sensor arrangement for determining a target-gas concentration.

BACKGROUND OF THE INVENTION

The invention relates to a gas-sensor arrangement for measuring a target-gas concentration with a radiation emitter, by means of which radiant energy can be irradiated through a space containing the target gas, a radiation receiver, by means of which radiant energy irradiated by the radiation emitter can be detected, a filter that is assigned to the radiation receiver and that is permeable to radiation of a wavelength range corresponding to the target gas, and a controller that is connected to the radiation receiver and by means of which the target-gas concentration can be calculated on the basis of a detector signal applied by the radiation receiver to the controller.

Such gas-sensor arrangements are increasingly being used to monitor air quality, wherein in particular the quality of outdoor air and/or the quality of air present in internal spaces, in particular also passenger compartments of vehicles, is monitored.

For the monitoring of air quality in internal spaces, it should be ensured that any deterioration in this air quality can be responded to with suitable measures.

In the area of vehicles, use has for some time been made of gas-sensor arrangements suitable for this purpose, which include metal oxide sensors (MOS), by means of which the air is monitored for the presence of VOC (volatile organic compounds). In the case of excessively high concentrations of these VOC in the air present in the passenger compartment of the vehicle, it is possible by using such gas-sensor arrangements for the vehicle ventilation system to be switched on automatically in order to provide an exchange of air.

Use is increasingly being made of air-conditioning systems in motor vehicles, wherein carbon dioxide ($CO_2$) is used as a refrigerant. Since carbon dioxide, when its concentration increases in the passenger compartment air, can lead to tiredness and sleepiness on the part of the vehicle driver, gas-sensor arrangements are also used to monitor leakages in the air-conditioning system. In these cases, the gas-sensor arrangement constituted as a $CO_2$ sensor arrangement is intended, in the case inadmissible $CO_2$ concentrations in the passenger compartment air, to trigger an alarm or to act on a control device of a vehicle ventilation system with the aim of eliminating the hazard due to an excessively high $CO_2$ content in the passenger compartment air. This could be brought about for example by increasing the air throughput in the vehicle passenger compartment, as a result of which the $CO_2$ concentration inside the vehicle passenger compartment is reduced.

A method for monitoring the air quality in a vehicle passenger compartment is known from DE 10 2004 024 284 A1, wherein a hazard prevention for living creatures that are present in the passenger compartment of a parked car is intended to be provided by a gas-sensor arrangement suitable for detecting $CO_2$. Here, the passenger compartment temperature is also monitored apart from the $CO_2$ content of the passenger compartment air. If, in the presence of a comparatively high passenger compartment temperature, a predefined $CO_2$ increase gradient is detected, it is assumed that a living creature, e.g. a child or a domestic animal, is present in the passenger compartment of a motor vehicle. Here, the $CO_2$ increase gradient is characteristic of the fact that breathing is occurring in the passenger compartment of the motor vehicle.

OBJECT OF THE INVENTION

Proceeding from the above-described prior art, the problem underlying the invention is to make available a gas-sensor arrangement for measuring a target-gas concentration that can be implemented with a comparatively low technical-structural outlay and that can bring about an extremely reliable and accurate performance of measurements, especially in states in which measures for hazard prevention are required.

SUMMARY OF THE INVENTION

According to the invention, this problem is solved by the fact that the gas-sensor arrangement is constituted as a non-dispersive infrared spectrometry (NDIR) gas-sensor arrangement with an infrared radiation emitter as the radiation emitter and an infrared radiation receiver as the radiation receiver and that the infrared radiation emitter of the NDIR gas-sensor arrangement can be operated with different powers.

Since the gas-sensor arrangement according to the invention is constituted as an NDIR gas-sensor arrangement, performance with a higher degree of reliability and accuracy can be guaranteed, since the cross-sensitivity of NDIR gas-sensor arrangements to gases not relevant to the measurement and in particular to air humidity is very small compared to other gas-sensor arrangements provided for the relevant applications here, in particular gas-sensor arrangements with metal oxide sensors.

The NDIR gas-sensor arrangement includes the infrared radiation emitter and the infrared radiation receiver. The filter sits in front of the infrared radiation receiver, said filter permitting only the wavelength of interest for the given measurement purpose to pass to the infrared radiation receiver. This wavelength is dependent on the target gas to be monitored. In the case of an NDIR gas-sensor arrangement for the detection of the $CO_2$ content, this wavelength lies for example at 4.26 μm, since one of the absorption bands of $CO_2$ lies here. If the NDIR gas-sensor arrangement is used for the monitoring of HC (hydrocarbons), a wavelength of for example 3.3 μm is selected.

The energy transmitted by the infrared radiation emitter to the infrared radiation receiver is measured by the infrared radiation receiver of the NDIR gas-sensor arrangement. When the target gas to be detected with regard to its concentration enters into the beam path between the infrared radiation emitter and the infrared radiation receiver, part of the radiant energy on the specific wavelength is absorbed by the target gas present in the radiation path. According to the Lambert-Beer law, amongst others, this absorption is dependent on the mean optical path length of the measurement distance between the infrared radiation emitter and the infrared radiation receiver and on the concentration of the target gas. The Lambert-Beer law reads:

$$I = I_0 \cdot 10^{-\epsilon \cdot c \cdot d}$$

where $I_0$ the energy transmitted without target gas c the target-gas concentration d the mean optical path length of the measurement distance between the infrared radiation emitter and the infrared radiation receiver and ε a constant dependent on the target gas.

Target-gas concentration c is determined according to the above-described formula. In the ideal case, $I_0$, d and ? are constant. In this case, it would be sufficient to measure transmitted energy I with the infrared radiation receiver and to calculate target-gas concentration c with the aid of the formula. The higher the target-gas concentration c is, the less energy is transmitted. This is important, since all influences leading to a reduction in the energy transmission result in values for target-gas concentration c being outputted that are too high. A basic prerequisite for an exact measurement result is a radiant power of the infrared radiation emitter that is constant even over a very long period on the specific wavelength for the intended measurement. The mean optical path length of the measurement distance between the infrared radiation emitter and the infrared radiation receiver must not change either.

If, for example, reflecting surfaces are used to increase the signal quality of the detector signal of the NDIR gas-sensor arrangement, so that a greater part of the radiant energy emitted by the infrared radiation emitter can focus on the infrared radiation receiver, it is of great importance that the reflection properties of the materials constituting the reflecting surfaces are stable and do not change even over a possibly protracted service live of the NDIR gas-sensor arrangement. A decrease in the reflexivity or also a decrease in the radiant power of the infrared radiation emitter would otherwise always be interpreted as an excessively high target-gas concentration. Depending on the use of the NDIR gas-sensor arrangement according to the invention, a false alarm could possibly be triggered in this case, which of course should be prevented.

It is known from the prior art, for example, to operate the infrared radiation emitter in a pulsed manner in order to reduce the ageing of the infrared radiation emitter of the NDIR gas-sensor arrangement and also to reduce the consumption of electrical energy of the NDIR gas-sensor arrangement. For example, it is sufficient for some applications and purposes for an updated measurement value to be available every 5 seconds. The infrared radiation emitter is then switched on only every 5 seconds until such time as it has reached its full radiant power. 500 to 1000 milliseconds are often sufficient for this purpose. Following a fixed time interval, the reception power at the infrared radiation receiver is then measured, wherein the target-gas concentration is calculated from the detector signal resulting therefrom in the downstream controller.

If the NDIR gas-sensor arrangement is operated with a battery as a source of electrical energy, the pulsed operating mode known from the prior art is associated with a—for many applications—excessively high energy consumption. To solve this problem, provision is made in the case of the NDIR gas-sensor arrangement according to the invention such that the infrared radiation emitter of the NDIR gas-sensor arrangement can be operated with different powers. A considerable additional energy saving is thereby enabled.

Thus, for example, in the case where the NDIR gas-sensor arrangement is used for $CO_2$ leakage detection of a motor vehicle air conditioning system, an alarm threshold value is expedient and advisable that lies above a target gas or $CO_2$ concentration of 10000 ppm (1.0 volume-%). The upper limit of the measurement range advisable for these purposes then often lies above 100000 ppm (10.0 volume-%).

If it is to be detected whether a living creature is present inside an internal space, a wholly different measurement range of the NDIR gas-sensor arrangement is required than for the above-described $CO_2$ leakage detection of an air conditioning system. If the NDIR gas-sensor arrangement is used for the detection of the presence of living creatures inside an internal space, a high resolution and accuracy of the detection signal characterizing the $CO_2$ concentration in a concentration range up to 1000 ppm (0.1 volume-%) is required. This will be illustrated in the following example:

A sleeping infant draws breath approx. 20 times per minute. The air volume per breath amounts to approx. 100 ml. Per minute, the infant correspondingly exhales—with an enrichment of the respiratory air of 0.04 volume-% $CO_2$— 0.08 l $CO_2$. In one hour, this is approx. 5 l $CO_2$.

If the internal space to be monitored has a volume of approx. 5 $m^3$, i.e. 5000 l, the infant has caused an increase in the $CO_2$ concentration of 0.1 volume-% $CO_2$ after an hour. If it is assumed from this that a motor vehicle in the blazing sun reaches critical temperatures above 60 degrees C. in the passenger compartment within half an hour, the NDIR gas-sensor arrangement must be able to reliably detect an increase of the $CO_2$ concentration of 0.05 volume-% $CO_2$ (500 ppm). Without the operation of the infrared radiation emitter of the NDIR gas-sensor arrangement with different powers, as provided according to the invention, an NDIR gas-sensor arrangement known from the prior art would have a resolution that was far too low in a measurement range between 400 ppm and 5000 ppm.

To explain the advantages of the NDIR gas-sensor arrangement according to the invention, reference should additionally be made to the fact that one of the main energy consumers of such a NDIR gas-sensor arrangement is the infrared radiation emitter. For an NDIR gas-sensor arrangement with a particularly low energy consumption, therefore, the mode of operation of the infrared radiation emitter, such as it is known from the prior art, has to be changed. The pre-requisite for this is that the radiant energy received in the infrared radiation receiver of the NDIR gas-sensor arrangement is proportional to the radiant energy irradiated by the infrared radiation emitter. The radiant energy irradiated by the infrared radiation emitter is in turn directly dependent on the electrical energy used to operate the infrared radiation emitter.

A comparatively large amount of irradiated radiant energy thus also signifies a comparatively high amount of received radiant energy and therefore a comparatively large or distinct detector signal of the infrared radiation receiver. Such a comparatively large detector signal improves the signal-to-noise ratio, so that the measurement result is more accurate and has a better resolution.

Radiant energy W transmitted by the infrared radiation emitter to the infrared radiation receiver is proportional to the product of irradiated power $I_0$ and radiation duration T. In order to improve the signal quality, the irradiated power and/or the radiation duration could be increased. In order to reduce the energy consumption of the NDIR gas-sensor arrangement, the radiant power and/or the radiation duration could be reduced. Here, the size of the reduction could be worked out until the detector signal emitted by the infrared radiation receiver just still met the imposed requirements with regard to resolution, accuracy and signal-to-noise ratio. For this purpose, the NDIR gas-sensor arrangement according to the invention comprises a controller, by means of which the infrared radiation emitters can be operated with different radiant powers. For this purpose, a voltage supply provided for the energy supply of the infrared radiation emitter can be adjustable, wherein the adjustment takes place by the controller. Various steps of the radiant power of the infrared radiation emitter can be adjusted via the level of the given operating voltage of the voltage supply.

The NDIR gas-sensor arrangement according to the invention can expediently be operated in at least two operating modes, wherein the infrared radiation emitter is operated with a very low power in a first operating mode and the infrared radiation emitter is operated at high power in a second operating mode. The NDIR gas-sensor arrangement according to the invention has a comparatively low energy consumption in the first operating mode. In this operating mode, a reduced signal quality and therefore sacrificing a comparatively high resolution, accuracy and signal-to-noise ratio is consciously accepted. The comparatively low energy consumption has priority in this operating mode.

In the second operating mode, the NDIR gas-sensor arrangement according to the invention is operated with a comparatively high energy consumption. In this second operating mode, the priority is placed on a comparatively high quality of the detector signal, i.e. on a high resolution, a high accuracy and a high signal-to-noise ratio thereof.

As already mentioned above, it is known from the prior art to operate the infrared radiation emitter of the NDIR gas-sensor arrangement at intervals in order to reduce the energy consumption of the latter. If a low measuring rate is sufficient, the infrared radiation emitter is switched on briefly just to carry out each individual measurement. The infrared radiation emitter is switched off between the measurements and does not therefore require any electrical energy. The known interval operation also has the advantage that, during the times when the infrared radiation emitter is switched off, the signal of the infrared radiation receiver of the NDIR gas-sensor arrangement can be detected as a reference point for the following signal evaluation.

As already mentioned, there are applications in which a minimal energy consumption has to be achieved with a predetermined minimum measuring rate, e.g. in the case of the $CO_2$ leakage detection of an air conditioning system, which is operated with $CO_2$ as a refrigerant, in a parked motor vehicle. Here, the alarm threshold lies for example at a $CO_2$ concentration of 30000 ppm in the passenger compartment air of the motor vehicle. The alarm should be triggered at the alarm threshold value, with a permitted inaccuracy of a few percent. The basic content of $CO_2$ in the air stands at approx. 380 ppm. In a passenger car occupied by several occupants or persons, the $CO_2$ concentration can also reach values of 1900 ppm. The distance from the above-described alarm threshold value of approx. 30000 ppm, however, is in any event still marked. The factor is greater than 15 in the example described above.

By way of example, the mean current consumption of 50 µA at 12 V DC (W=0.6 M WH) must not be exceeded in a parked motor vehicle in the rest mode. At the same time, however, a minimum measuring rate of one measurement per minute should be achieved. Only 0.6 m WH/60=0.01 MWH of electrical energy is thus unavailable for each measurement. An infrared radiation emitter with a nominal power of 400 mW could be operated for 90 ms with this available electrical energy. A typical infrared radiation emitter when used for NDIR, however, reaches its operating temperature and therefore its full radiant power only after several 100 milliseconds. The reduction in the radiation duration of for example 300 ms in the already described second operating mode to 90 ms in the already described first operating mode thus means a marked reduction in the radiant power and therefore a marked reduction in the signal quality. The required measurement tolerances in respect of the alarm threshold value thus cannot be achieved. The achievement of these measurement tolerances is achieved with the NDIR gas-sensor arrangement according to the invention solely by the fact that the infrared radiation emitter of the NDIR gas-sensor arrangement can be operated with different powers.

According to an advantageous development of the NDIR gas-sensor arrangement according to the invention, provision is made such that the NDIR gas-sensor arrangement can be switched from the first operating mode into the second operating mode by its controller depending on detector signals detected in the latter in the first operating mode of the NDIR gas-sensor arrangement.

The switch from the first into the second operating mode can be provided particularly when it is detected in the controller that a presettable threshold value of the target-gas concentration is reached or exceeded.

According to a further expedient development of the NDIR gas-sensor arrangement according to the invention, the latter can be switched by its controller from the first operating mode into the second operating mode when it is detected in the controller that a presettable threshold value of the gradient or the increase in the target-gas concentration is reached or exceeded.

For hazard prevention, it may expediently be advantageous to put an alarm system and/or a ventilation device or suchlike into operation by the controller of the NDIR gas-sensor arrangement if, in the second operating mode of the NDIR gas-sensor arrangement, the controller determines that a presettable alarm threshold value is reached or exceeded.

In order to ensure that the NDIR gas-sensor arrangement according to the invention is operated, whenever reasonably possible, in its first operating mode accompanied by a low energy consumption, it is advantageous if the NDIR gas-sensor arrangement according to the invention can be put back from its second into its first operating mode by its control and evaluation unit if, in the second operating mode of the NDIR gas-sensor arrangement, it is detected by the controller that the threshold value set for the switch from the first into the second operating mode of the NDIR gas-sensor arrangement or another threshold value set for a switch from the second into the first operating mode is reached or fallen below.

In order to prevent constant switching from the first into the second operating mode and vice versa in certain applications, it is advantageous if the threshold value presettable for the first operating mode for switching into the second operating mode and the threshold value presettable for the second operating mode for switching into the first operating mode of the NDIR gas-sensor arrangement can be adapted by the controller of the NDIR gas-sensor arrangement according to the invention if, in the second operating mode of the NDIR gas-sensor arrangement, it is detected by the controller that the presettable alarm threshold value is not reached during a presettable period following the switch from the first into the second operating mode of the NDIR gas-sensor arrangement.

The NDIR gas-sensor arrangement according to the invention described above can, as already explained above, be advantageously used for the detection of the $CO_2$ concentration or the HC concentration in the passenger compartment of a motor vehicle.

In a method according to the invention for the operation of an NDIR gas-sensor arrangement, preferably an NDIR gas-sensor arrangement in one of the embodiments described above, at least two operating modes of the NDIR gas-sensor arrangement are provided, wherein an infrared radiation emitter of the NDIR gas-sensor arrangement is operated with a different power in each operating state of the NDIR gas-sensor arrangement, and wherein the infrared radiation emitter is operated at low power in a first operating mode and the infrared radiation emitter is operated at high power in a second operating mode.

For the implementation of the method according to the invention described above for the operation of an NDIR gas-sensor arrangement, provision is expediently made such that switching of the NDIR gas-sensor arrangement from one operating mode into another is always carried out when presettable threshold values are reached or fallen below or exceeded.

BRIEF DESCRIPTION OF THE DRAWING

The invention is explained below in greater detail with the aid of an embodiment making reference to the drawing, in the single FIGURE whereof an example of embodiment of a gas-sensor arrangement according to the invention for measuring a target-gas concentration is represented in principle.

SPECIFIC DESCRIPTION OF THE INVENTION

An embodiment of a gas-sensor arrangement 1 shown in the single FIGURE is used to measure a target-gas concentration, e.g. inside a space 2. Space 2 can for example be passenger compartment 2 of a motor vehicle.

Gas-sensor arrangement 1 is constituted as a non-dispersive infrared spectroscopy (NDIR) gas-sensor arrangement 1 and comprises an infrared radiation emitter 3, by means of which infrared radiant energy can be irradiated through space or passenger compartment 2 containing a target gas, e.g. carbon dioxide ($CO_2$).

An infrared radiation receiver 4 is disposed at a distance from infrared radiation emitter 3 of NDIR gas-sensor arrangement 1. Infrared radiant energy irradiated by infrared radiation emitter 3 through space or passenger compartment 2 can be detected by infrared radiation receiver 4.

Disposed in the radiation path between infrared radiation emitter 3 on the one hand and infrared radiation receiver 4 on the other hand is a filter 5 that is assigned to infrared radiation receiver 4 and is designed permeable to radiation of a wavelength range that corresponds to the target gas. In this regard, a wavelength range of approx. 4.26 µm is selected in the case where $CO_2$ is provided as the target gas, since one of the absorption bands of $CO_2$ lies here. If hydrocarbons (HC) are present as the target gas, a wavelength range of for example 3.3 µm is selected for this purpose.

Both infrared radiation emitter 3 and infrared radiation receiver 4 of NDIR gas-sensor arrangement 1 are connected to a controller 6. The target-gas concentration can be calculated in controller 6 on the basis of a detector signal that is applied by infrared radiation receiver 4 to controller 6.

Moreover, by means of controller 6 of NDIR gas-sensor arrangement 1, its infrared radiation emitter 3 can be operated with different powers.

Furthermore, in the represented example of embodiment, an alarm system 7 and a ventilation device 8 are connected to controller 6 of NDIR gas-sensor arrangement 1. In the case where the value calculated for the target-gas concentration in controller 6 exceeds a presettable limiting value, alarm system 7 is operated by controller 7, so that hazards to persons present in space or passenger compartment 2 can be reduced or prevented. In addition or alternatively, controller 6 can also put ventilation device 8 into operation when the limiting value is reached or exceeded, wherein the target-gas concentration inside space or inside passenger compartment 2 can be brought back into a permitted range by the operation of ventilation device 8.

In the represented example of embodiment, NDIR gas-sensor arrangement 1 shown in the FIGURE can be operated in two different types of operation or operating modes. In a first operating mode, NDIR gas-sensor arrangement 1 is operated with a comparatively low energy consumption. In this first operating mode, a reduced signal quality and therefore sacrificing a comparatively high resolution, accuracy and signal-to-noise ratio is consciously accepted. The priority of this first operating mode is given to the comparatively low energy consumption.

In the second operating mode, the operation of NDIR gas-sensor arrangement 1 is accompanied by a comparatively high energy consumption. In this second operating mode, the priority is placed on a comparatively high signal quality with high resolution, high accuracy and high signal-to-noise ratio.

In the first operating more, infrared radiation emitter 3 of NDIR gas-sensor arrangement 1 is operated by controller 6 at low power. In the second operating mode, infrared radiation emitter 3 is correspondingly operated by controller 6 at high power.

The change from the first operating mode into the second operating mode and vice versa is essential for the operation of NDIR gas-sensor arrangement 1.

For this purpose, a presettable first threshold value of the target-gas concentration is stored in controller 6. This first threshold value of the target-gas concentration is set so low compared to a likewise presettable alarm threshold value that, on account of the distance between this first threshold value and the alarm threshold value, it is in any event ensured that the switch from the first operating mode into the second operating mode takes place long before the alarm threshold value of the target-gas concentration is reached.

If, in the first operating mode of NDIR gas-sensor arrangement 1, the controller determines 6 that the target-gas concentration reaches or exceeds the presettable first threshold value, switching of NDIR gas-sensor arrangement 1 out of the first operating mode into the second operating mode takes place by controller 6. Infrared radiation emitter 3 is operated with a much higher radiant power in the second operating mode of NDIR gas-sensor arrangement 1. It is thus ensured that the quality of the detector signal emitted by infrared radiation receiver 4 to controller 6 is considerably improved in the second operating mode, and more precisely in a range of the target-gas concentration that lies well away from a hazard range.

If the target-gas concentration in space or passenger compartment 2 increases in the second operating mode of the NDIR gas-sensor arrangement 1 to the presettable alarm threshold value or if it exceeds it, alarm system 7 is operated by controller 6, wherein ventilation device 8 can be put into operation at the same time, by means of which it can be ensured by ventilation of space or passenger compartment 2 that a further increase in the target-gas concentration is prevented.

If, in NDIR gas-sensor arrangement 1 running in the second operating mode, a third threshold value also presettable for the target concentration and storable in controller 6 is fallen below, controller 6 switches NDIR gas-sensor arrangement 1 back into the first operating mode.

If, after switching of NDIR gas-sensor arrangement 1 into its second operating mode, the preset threshold value stored in controller 6 is not reached, a new first threshold value is calculated that lies above the old first threshold value; this new first threshold value is stored in controller 6, after which NDIR gas-sensor arrangement 1 is switched back into the first operating mode by controller 6. Through this adaptation or increase in the first threshold value, which is provided for switching NDIR gas-sensor arrangement 1 out of its first into its second operating mode, NDIR gas-sensor arrangement 1 is thus prevented from changing continually between the first and the second operating mode.

In the operation of NDIR gas-sensor arrangement 1 described above, a situation is achieved whereby, for the overwhelming part of the service life thereof, its infrared radiation emitter 3 can be operated with a very low electrical power requirement. The radiant power of infrared radiation emitter 3 of NDIR gas-sensor arrangement 1 is increased only in the comparatively rare cases in which the presettable first threshold value of the target-gas concentration is exceeded. Only then is the detector signal with an increased signal quality required, wherein this increased signal quality is ensured by the then considerably increased radiant power of infrared radiation emitter 3 of NDIR gas-sensor arrangement 1.

The invention claimed is:

1. A gas-sensor arrangement for measuring a target-gas concentration, the arrangement comprising:
   a variable-power infrared-radiation emitter that can project radiant energy in a first operating mode at a low power and in a second operating mode at a high power from one side of a space containing the target gas and through the space to the other side thereof;
   a infrared-radiation receiver on the other side of the space and positioned to be irradiated by the radiant energy projected by the emitter through the space for emitting a signal corresponding to radiation received;
   a filter between the receiver and the space and permeable only to radiation of a wavelength range that corresponds to the target gas; and
   a controller connected to the radiation receiver for calculating the target-gas concentration on the basis of the signal from the receiver and for, when in the first operating mode, switching the emitter from the first operating mode to the second operating modes in dependence on detector signals detected in the controller.

2. The gas-sensor arrangement defined in claim 1, wherein the controller switches the emitter from the first operating mode to the second operating mode on detection in the controller that a presettable threshold value of the target-gas concentration is reached or exceeded.

3. The gas-sensor arrangement defined in claim 1, wherein the controller switches the emitter from the first operating mode to the second operating mode on detection in the controller that a presettable threshold value of a gradient or rate of increase in the target-gas concentration is reached or exceeded.

4. The gas-sensor arrangement defined in claim 1, further comprising:
   an alarm system or a ventilation device operable in the second operating mode of the of the emitter when the controller determines that a presettable alarm threshold value is reached or exceeded.

5. The gas-sensor arrangement defined in claim 1, wherein the controller can switch the NDIR gas-sensor arrangement from the second operating mode into it's the first operating mode if, in the second operating mode of the NDIR gas-sensor arrangement, the controller detects that a threshold value set for switching from the first into the second operating mode of the NDIR gas-sensor arrangement or another threshold value set for switching from the second into the first operating mode is reached or fallen below.

6. The gas-sensor arrangement defined in claim 1, wherein the controller adjusts the threshold value for switching from the first operating mode into the second operating mode or the threshold value for switching from the second operating mode into the first operating mode of the emitter if, in the second operating mode of the emitter, the controller detects that a presettable alarm threshold value is not reached during a presettable period following switching from the first operating mode into the second operating mode of the emitter.

7. Use of a gas-sensor arrangement defined in claim 1 for the detection of the $CO_2$ concentration or the HC concentration in the passenger compartment of a motor vehicle.

8. The gas-sensor arrangement defined in claim 1, wherein in the signal-to-noise ratio of the signal from the emitter is significantly higher in the first low-power operating mode than in the second high-power operating mode.

9. The gas-sensor arrangement defined in claim 8 wherein the controller only triggers an action when a predetermined threshold is reached or passed when operating in the second high-power mode.

10. A gas-sensor arrangement for measuring a target-gas concentration, the arrangement comprising:
    a variable-power infrared-radiation emitter that can project radiant energy in a low-power operating mode with low resolution and signal quality and in a high-power operating mode power with high resolution and signal quality from one side of a space containing the target gas and through the space to the other side thereof;
    a infrared-radiation receiver on the other side of the space and positioned to be irradiated by the radiant energy projected by the emitter through the space for emitting a signal corresponding to radiation received;
    a filter between the receiver and the space and permeable only to radiation of a wavelength range that corresponds to the target gas; and
    a controller connected to the radiation receiver for calculating the target-gas concentration,
       switching the emitter from the low-power operating mode to the high-power operating modes when the detector signals indicate that a presettable threshold value of the target-gas concentration is reached or passed, and
       initiating an action when, in the high-power operating mode, the detector signals indicate that another presettable threshold value of the target-gas concentration is reached or passed.

* * * * *